U S008573052B2

(12) United States Patent
Hong et al.

(10) Patent No.: US 8,573,052 B2
(45) Date of Patent: Nov. 5, 2013

(54) CAPACITIVE HUMIDITY SENSOR AND MANUFACTURING METHOD

(75) Inventors: Sung Min Hong, Yongin-si (KR); Kun Nyun Kim, Yongin-si (KR); Young Chang Jo, Suwon-si (KR); Won Hyo Kim, Yongin-si (KR)

(73) Assignee: Korea Electronics Technology Institute, Seongnam-si, Gyeonggi-do (KR)

( * ) Notice: Subject to any disclaimer, the term of this patent is extended or adjusted under 35 U.S.C. 154(b) by 327 days.

(21) Appl. No.: 13/128,934

(22) PCT Filed: Nov. 12, 2009

(86) PCT No.: PCT/KR2009/006654
§ 371 (c)(1),
(2), (4) Date: Jul. 13, 2011

(87) PCT Pub. No.: WO2010/056049
PCT Pub. Date: May 20, 2010

(65) Prior Publication Data
US 2011/0259099 A1    Oct. 27, 2011

(30) Foreign Application Priority Data

Nov. 12, 2008    (KR) .................... 10-2008-0112057

(51) Int. Cl.
*G01N 19/00* (2006.01)
(52) U.S. Cl.
USPC ...................................................... 73/335.04
(58) Field of Classification Search
USPC ................... 73/29.01, 29.02, 335.01–335.05; 422/83, 88
See application file for complete search history.

(56) References Cited

U.S. PATENT DOCUMENTS

| 4,975,249 | A   | * | 12/1990 | Elliott ............................. 422/83 |
| 7,481,107 | B2  | * | 1/2009  | Itakura et al. ............... 73/335.02 |
| 2004/0155751 | A1 |   | 8/2004  | Benzel et al. |
| 2007/0107500 | A1 | * | 5/2007  | Patel ................................ 73/73 |
| 2007/0131020 | A1 | * | 6/2007  | Itakura et al. ................ 73/29.02 |

FOREIGN PATENT DOCUMENTS

| JP | 4110648    | 4/1992  |
| JP | 9-12720 A  | 5/1997  |
| JP | 3453962    | 5/1997  |
| JP | 10-213470 A | 8/1998 |
| JP | 3457826    | 8/1998  |
| JP | 2004535589 | 11/2004 |
| JP | 2008070353 | 3/2008  |
| JP | 2011536242 | 4/2012  |

(Continued)

OTHER PUBLICATIONS

International Search Report mailed Jul. 1, 2010 for PCT/KR2009/006654.

(Continued)

*Primary Examiner* — Hezron E Williams
*Assistant Examiner* — Nathaniel Kolb
(74) *Attorney, Agent, or Firm* — Lowe Hauptman & Ham LLP

(57) ABSTRACT

A capacitive humidity sensor, and more particularly, to a capacitive humidity sensor and a manufacturing method thereof capable of increasing reliability of the sensor by forming a dehumidification layer of a polymer material having a large surface area between a lower electrode layer and an upper electrode layer while miniaturizing the humidity sensor by forming a sensor unit on an ROIC substrate.

11 Claims, 11 Drawing Sheets

(56) References Cited

FOREIGN PATENT DOCUMENTS

| KR | 10-2005-0041325 A | 5/2005 |
| KR | 10-2008-0058286 A | 6/2008 |
| KR | 2009-0029383 | 3/2009 |

OTHER PUBLICATIONS

International Search Report dated Jul. 1, 2010 from PCT/KR2009/006654.

* cited by examiner

CAPACITIVE HUMIDITY SENSOR AND MANUFACTURING METHOD

BACKGROUND

1. Field of the Disclosure

The present disclosure relates to a capacitive humidity sensor, and more particularly, to a capacitive humidity sensor and a manufacturing method thereof capable of increasing reliability of the sensor by forming a dehumidification layer of a polymer material having a large surface area between a lower electrode layer and an upper electrode layer while miniaturizing the humidity sensor by forming a sensor unit on an ROIC substrate.

2. Discussion of the Background Art

Generally, a capacitive humidity sensor is manufactured so that a polymer layer for dehumidification is formed between electrodes at both ends thereof and a change in a charge amount induced to both ends of the electrode depends on a change in dielectric constant by the dehumidification of the polymer layer and a change in an induced charge accordingly.

The capacitive humidity sensor has more complicated manufacturing process and is more expensive than a resistive humidity sensor that uses a change in resistance according to a change in humidity due to voltage applied to both ends thereof to measure humidity. However, for the reason of high stability and reliability in characteristics, the capacitive humidity sensor has been mainly used for expensive measurement.

FIG. 1 shows a perspective view of a structure of a capacitive humidity sensor according to the related art.

An insulating layer 120 of $SiO_2$, $Si_3N_4$, $SiO_xN_y$, or the like is formed on a silicon substrate 110. Further, a sensor unit 160 and a readout integrated circuit (ROIC) 170 are formed on the silicon substrate on which the insulating film 120 is formed.

In reviewing a method of manufacturing the sensor unit 160, a lower electrode layer 130 is formed on the insulating layer 120 by depositing and patterning a metal layer such as aluminum (Al) and platinum (Pt). Then, a dehumidification layer 140 is formed on the lower electrode layer 130 by spin coating and patterning a polyimide (PI) layer and is subjected to heat treatment at a temperature between 200° C. to 300° C.

An upper electrode layer 150 in a comb shape is formed on the polyimide dehumidification layer 140 by depositing and patterning the metal layer of the same material as the lower electrode layer 130, thereby manufacturing the capacitive humidity sensor having a parallel plate capacitor structure in which the polyimide dehumidification layer 140 is formed between the upper electrode layer 150 and the lower electrode layer 130.

In this case, the reason of forming the upper electrode layer 150 in a comb shape differently from the lower electrode layer 130 is to smoothly pass water molecule into the polyimide dehumidification layer 140. That is, this is to partially expose the polyimide dehumidification layer 140.

After the sensor unit 160 is formed as described above, the ROIC 170 is formed on the silicon substrate in which the sensor unit 160 is not present. Since an electrical phenomenon such as current, voltage, or the like, that are generated by the ROIC 170 may affect the humidity sensor, it is preferable that the ROIC 170 is formed to be maintained at a predetermined distance from the sensor unit 160.

However, the capacitive humidity sensor according to the related art has a limitation in miniaturization of the humidity sensor since the sensor unit and the ROIC unit are horizontally positioned on a single substrate.

Further, the characteristics of the capacitive humidity sensor, such as sensitivity, are determined by unique characteristics of the polymer. Since the capacitive humidity sensor according to the related art has a sandwich structure in which the dehumidification layer of the polymer is inserted between both electrodes, thereby making it difficult to improve the sensitivity of the dehumidification layer.

The present disclosure has been made in an effort to provide a capacitive humidity sensor and a manufacturing method thereof capable of increasing reliability of the sensor by forming a dehumidification layer of a polymer material having a large surface area between a lower electrode layer and an upper electrode layer while miniaturizing the humidity sensor by forming a sensor unit on an ROIC substrate.

SUMMARY

An exemplary embodiment of the present disclosure, provides a capacitive humidity sensor, including: an ROIC substrate that includes an electrode pad; a metal layer that is formed on the ROIC substrate and patterned to partially expose the electrode pad; an insulating layer that is formed on the metal layer and patterned to partially expose the electrode pad; a lower electrode layer that is formed on the insulating layer; a dehumidification layer that is formed on the lower electrode layer to be etched so as to expand a surface area; an upper electrode layer formed on the dehumidification layer; and a connection layer that is formed on the exposed electrode pad and contacts each of the lower electrode layer and the upper electrode layer with the electrode pad.

The upper electrode layer may be formed on the region which is not etched in the dehumidification layer.

The dehumidification layer and the upper electrode layer may be patterned in a comb or branch shape.

30% to 70% of the thickness of the dehumidification layer may be etched.

The dehumidification layer may be made of a polyimide-based polymer.

The lower electrode layer may be formed on the insulating layer that is not patterned.

Another exemplary embodiment of the present disclosure, provides a manufacturing method of a capacitive humidity sensor, the method including: forming an insulating layer on the metal layer; patterning the insulating layer and the metal layer to partially expose the electrode pad; forming a lower electrode layer on the insulating layer; forming a dehumidification layer on the lower electrode layer; forming and patterning an upper electrode layer on the dehumidification layer; and etching the dehumidification layer by using the patterned upper electrode layer as a mask.

The dehumidification layer may be made of a polyimide-based polymer.

The upper electrode layer may be formed by being patterned in a comb or branch shape.

The dehumidification layer may be formed by etching 30% to 70% of a thickness thereof.

The lower electrode layer may be formed on the insulating layer that is not patterned.

According to the capacitive humidity sensor and the manufacturing method thereof of the present disclosure, the humidity sensor can be miniaturized by forming the sensor unit on the ROIC substrate.

In addition, the reliability of the sensor can be increased by improving the sensitivity due to the formation of the dehumidification layer of the polymer material having the increased surface area between the lower electrode layer and the upper electrode layer.

DETAILED DESCRIPTION OF THE PREFERRED EMBODIMENT

Terms and words used in the present specification and claims are not to be construed as a general or dictionary meaning but are to be construed meaning and concepts meeting the technical ideas of the present disclosure based on a principle that the inventors can appropriately define the concepts of terms in order to describe their own disclosures in best mode.

Therefore, configurations described in embodiments and shown in drawings of the present specification indicate only the most preferred example rather than indicating all the technical ideas of the present disclosure and therefore, it is to be understood that various equivalents and modifications that can replace the above configurations may be present.

Hereinafter, exemplary embodiments of the present disclosure will be described in detail with reference to the accompanying drawings.

Figure 1:
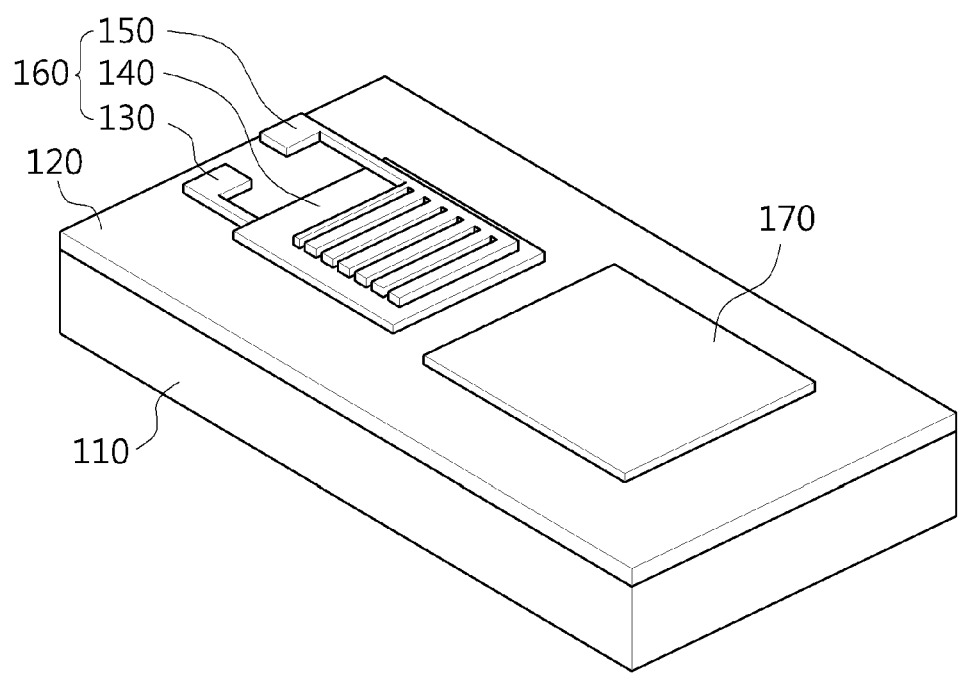
FIG. 1 is a perspective view of a capacitive humidity sensor according to the related art.
Figure 2:
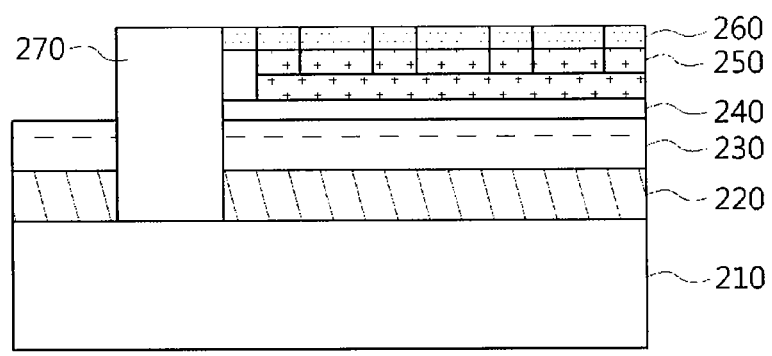
FIG. 2 is a cross-sectional view of a capacitive humidity sensor according to an exemplary embodiment of the present disclosure.

FIG. 2 shows a cross-sectional view of a capacitive humidity sensor according to an exemplary embodiment of the present disclosure.

A metal layer 220 is formed on an ROIC substrate 210 including an electrode pad (not shown) and an insulating layer 230 is formed on the metal layer 220. Further, the metal layer 220 and the insulating layer 230 are patterned so as to expose a portion of the electrode pad on the ROIC substrate.

A lower electrode layer 240 is formed on the insulating layer 230 that is not patterned and a dehumidification layer 250 patterned in a comb or branch shape is formed on the lower electrode layer 240. In this case, the etching depth of the dehumidification layer may be 30% to 70% of the entire thickness of the dehumidification layer 250.

Finally, after the upper electrode layer 260 is formed on the dehumidification layer 250 that is not etched, a connection layer 270 is formed so as to electrically connect the lower electrode layer 240 and the upper electrode layer 250 with the electrode pad formed on the ROIC substrate 210.

As described above, sensor units 240, 250, and 260 are formed on the ROIC substrate 210, thereby miniaturizing the humidity sensor. In addition, a larger amount of moisture in the air is absorbed into the dehumidification layer 250 by partially etching the dehumidification layer 250 so as to be exposed to the air, thereby forming the humidity sensor with the excellent humidity sensitivity.

FIGS. 3 to 9 show process flow charts of the capacitive humidity sensor according to an exemplary embodiment of the present disclosure.

Since the upper portion of the ROIC substrate 210 is manufactured by a microelectro mechanical systems (MEMS) process, the surface thereof is very rough. The roughness of the surface increases the specific surface area, which becomes a good condition to manufacture the humidity sensor.

The electrode pad (not shown) for connecting the upper electrode layer and the lower electrode layer, which are present in the sensor unit to be described below, with the ROIC is formed on the ROIC substrate 210.

Figure 3:
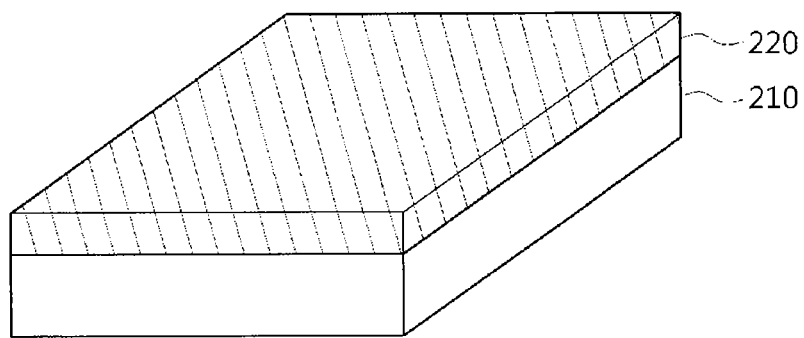
FIGS. 3 to 9 are process flow charts of the capacitive humidity sensor according to an exemplary embodiment of the present disclosure.

The surface that becomes rough by the MEMS process and the electrode pad may be flat covered with the metal layer 220 by forming the metal layer 220 on the ROIC substrate 210 (FIG. 3).

Figure 4:
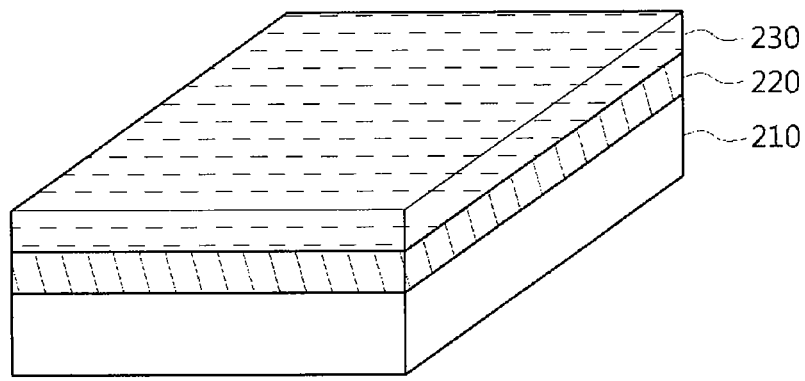

Further, the insulating layer 230 is formed on the metal layer 220 (FIG. 4). As the insulating layer 230, an oxide layer or a nitride layer of $SiO_2$, $Si_3N_4$, $SiO_xN_y$, or the like, may be formed to have a thickness of 2000 Å to 4000 Å and maintain an electrical insulating state with the lower electrode layer 240 that is formed by a post-process.

Further, the metal layer 220 and the insulating layer 230 are patterned so as to expose a portion of the electrode pad formed on the ROIC substrate (not shown). This is to contact the lower electrode layer 240 and the upper electrode layer 250 to be formed later with the ROIC.

Figure 5:
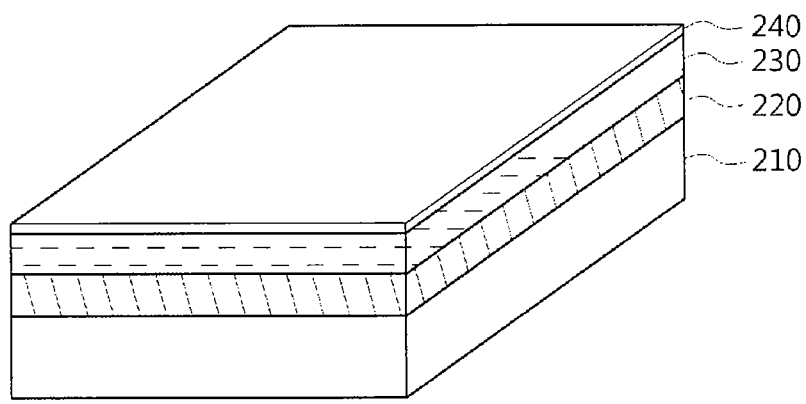

After the insulating layer 230 is patterned, the lower electrode layer 240 is formed in the upper region of the insulating layer 230 that is not patterned (FIG. 5). The lower electrode layer 240 is formed using any one of a vacuum vapor deposition method or a physical deposition method including sputtering. The lower electrode layer 240 may be formed as a thin film having the thickness of 500 Å to 1500 Å by using a material including a metal having excellent conductivity, such as aluminum (Al), gold (Au), platinum (Pt), or the like.

Figure 6:
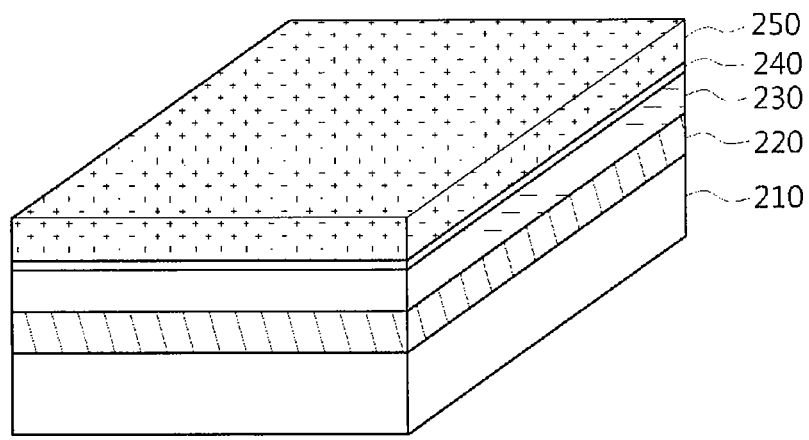

When the lower electrode layer 240 is formed, a polyimide-based polymer solution as the dehumidification layer 250 is spin-coated over the lower electrode layer 240 at a micro thickness. In this case, the thickness of the dehumidification layer 250 may be 0.1 µm to 0.5 µm (FIG. 6).

As the polymer solution according to the exemplary embodiment of the present disclosure, the polyimide solution may be used.

When the dehumidification layer 250 is applied, air in the film is removed by pre-annealing for 100 to 150 seconds at about 100° C. to 120° C. in vacuum. Further, when the pre-annealing completes, the post-heat treatment is performed. The temperature rises to 200° C. to 250° C. for 100 to 120 minutes under a nitrogen atmosphere. Next, the temperature is maintained to 200° C. to 250° C. for 30 to 40 minutes, the temperature rises to 300° C. to 350° C. for 60 to 80 minutes, and then, the post-heat treatment is performed. When the post-heat treatment completes, the polymer film is reduced by about 40% in thickness due to the evaporation of the solvent and is converted into a very thermally and chemically stable state.

Figure 7:
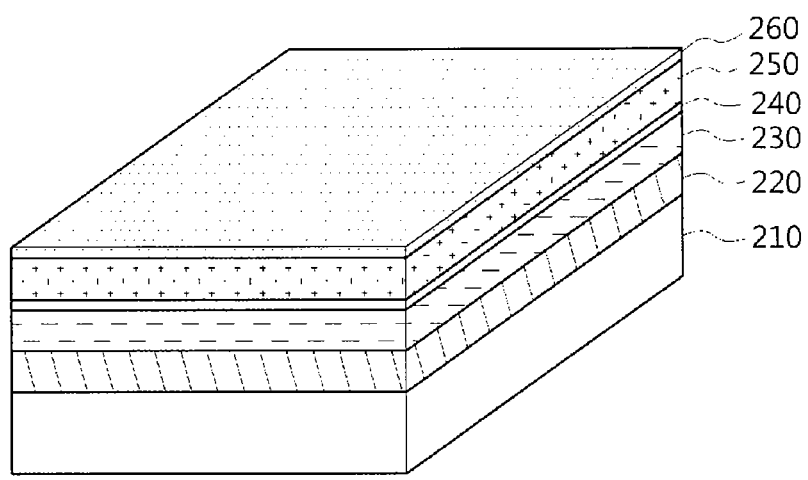

The upper electrode layer 260 is formed on the dehumidification layer 250, that is, the polyimide film that is subjected to the post-heat treatment (FIG. 7). The upper electrode layer 260 is also formed to have the thickness of 300 Å to 600 Å using the material including the metal having the excellent conductivity, such as aluminum (Al), gold (Au), Platinum (Pt), similar to the lower electrode layer 240.

In addition, in order to improve the adhesion with the dehumidification layer, a process of depositing a chromium layer (not shown) as the buffer layer at a thickness of 50 Å to 150 Å may be added.

Figure 8:
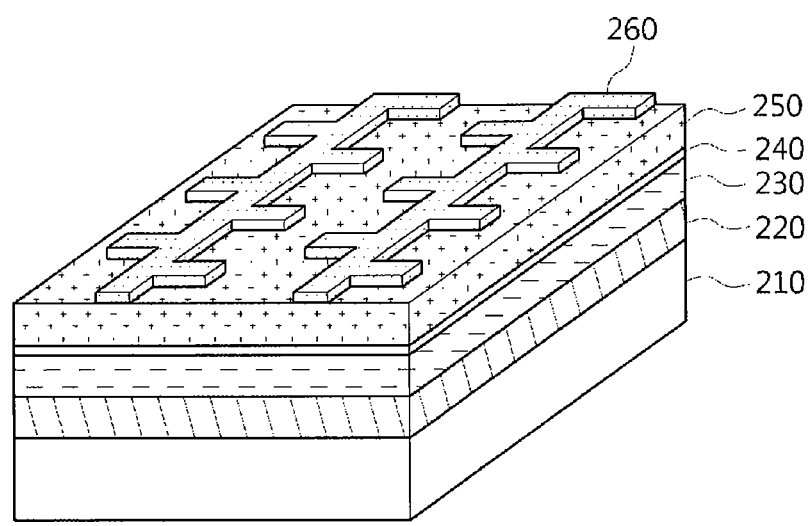

When the upper electrode layer 260 is formed, the upper electrode layer 260 is patterned by using photolithography (FIG. 8). In this case, the surface areas of the upper electrode layer 260 and the dehumidification layer 250 contacting moisture may be more exposed by forming the patterning shape in a comb or branch shape.

Figure 9:
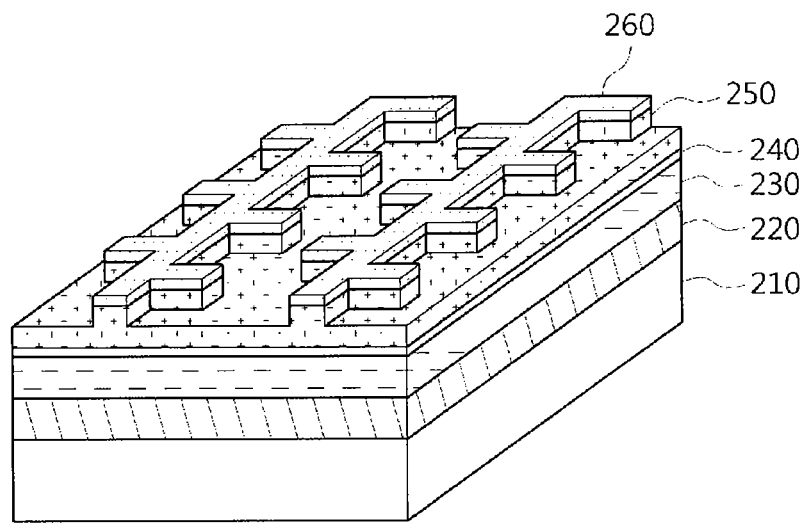

Further, a reactive ion etching (RIE) process of etching the entire surface of the dehumidification layer 250, which is exposed by using the patterned upper electrode layer 260 as a mask, by $O_2$ plasma is performed (FIG. 9). The ME etches the entire surface of the dehumidification layer 250 exposed by the photolithography of the upper electrode layer 260. The etching depth may be about 30% to 70% of the entire thickness of the humidification layer 250.

Figure 10:
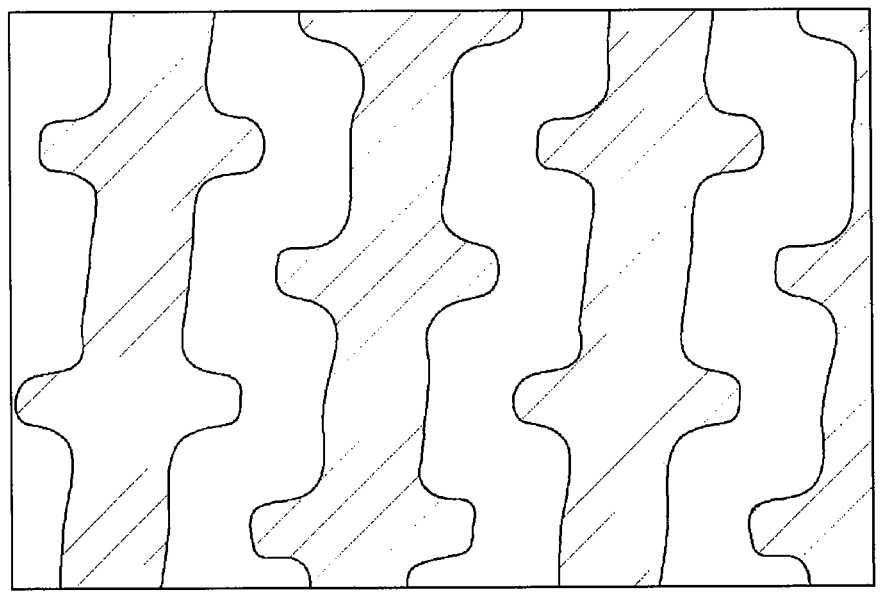
FIG. 10 is an image of a scanning electron microscope of the capacitive humidity sensor according to an exemplary embodiment of the present disclosure.

FIG. 10 is an image of a scanning electron microscope of the capacitive humidity sensor according to an exemplary embodiment of the present disclosure.

FIGS. 11 to 14 are graphs showing characteristics of the capacitive humidity sensor according to an exemplary embodiment of the present disclosure.

Figure 11:
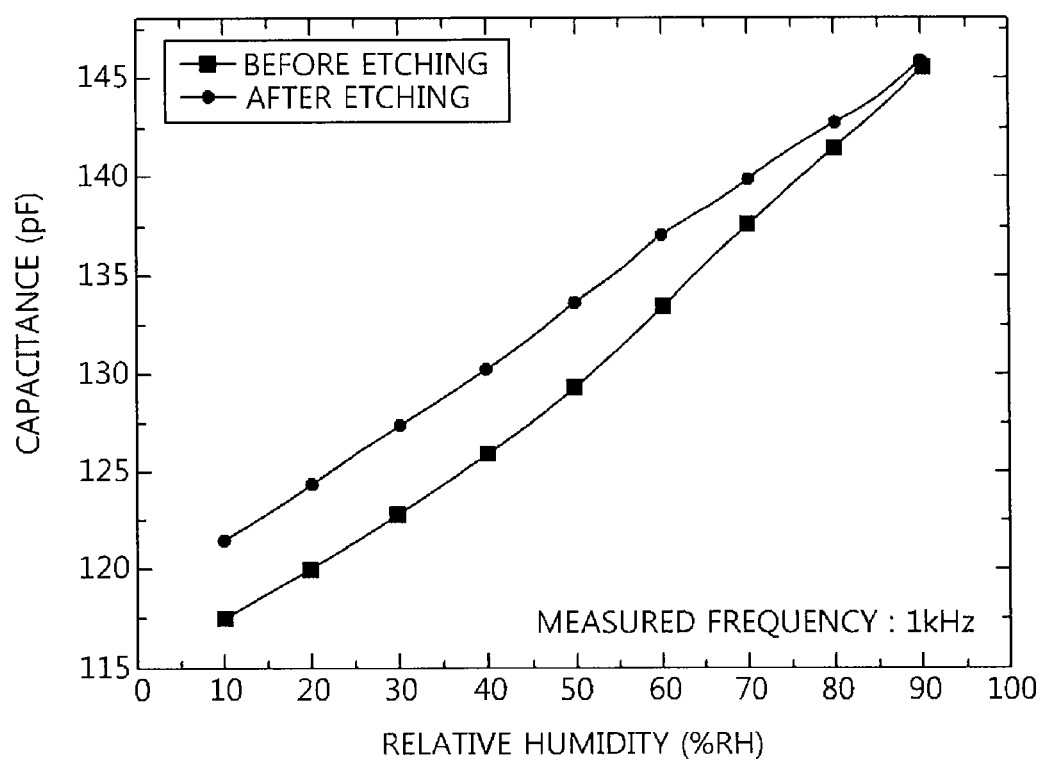
FIGS. 11 to 14 are graphs showing characteristics of the capacitive humidity sensor according to an exemplary embodiment of the present disclosure.

FIG. 11 shows capacitance of relative humidity of the capacitive humidity sensor according to whether the polyimide layer used as the dehumidification layer is etched.

The humidity sensor (FIG. 8) before the dehumidification layer is etched represents the humidity sensor in which only the upper electrode layer is patterned. Further, the humidity sensor (FIG. 9) after the dehumidification layer is etched represents one in which the dehumidification layer is etched at a predetermined thickness by using the patterned upper electrode layer as the mask.

The humidity sensitivity of the humidity sensor before the dehumidification layer is etched is 303 fF/% RH and the humidity sensitivity of the humidity sensor after etching the dehumidification layer is 350 fF/% RH. As a result, it may be appreciated that the humidity sensitivity of the humidity sensor in which the dehumidification layer is etched is increased by 15.5%.

When the dehumidification layer is etched, the etched surface is more exposed to the external air. Therefore, a larger amount of moisture in the air is absorbed into the dehumidification layer, such that the capacitance is increased.

That is, even though the same amount of moisture is present in the air according to whether the dehumidification layer is etched, the sensitivity sensing the moisture is changed. The humidity sensor with the more excellent humidity sensitivity may be formed when the dehumidification layer is etched.

Figure 12:
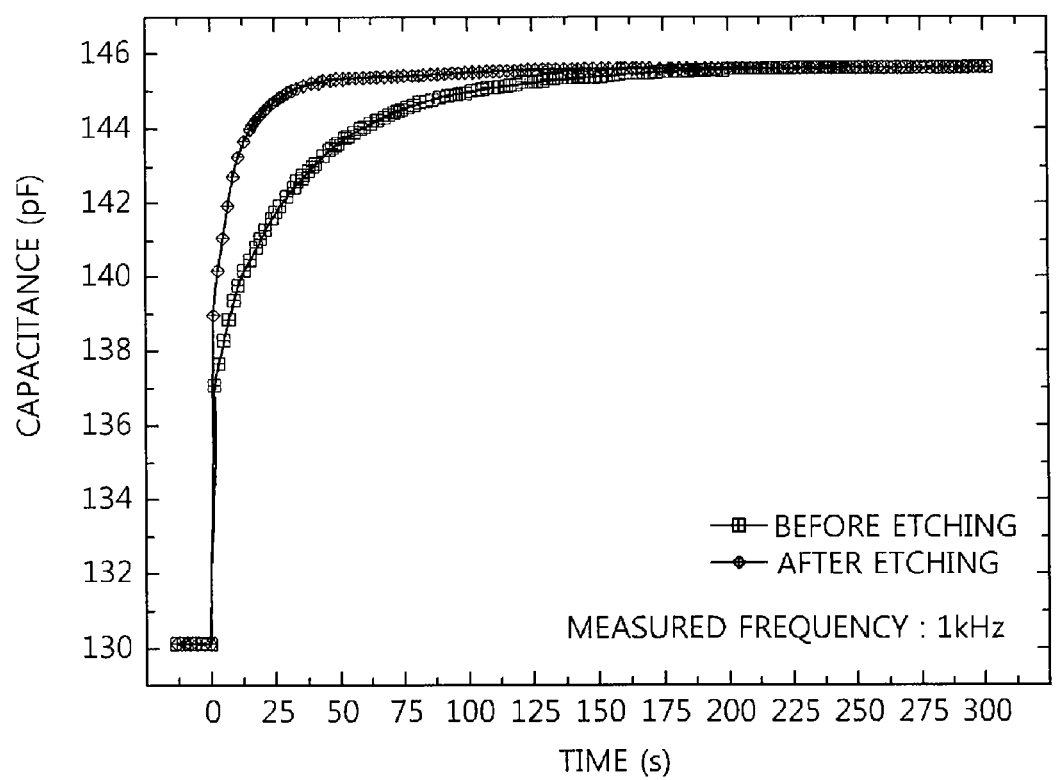

FIG. 12 shows the reaction rate for the moisture of the capacitive humidity sensor according to an exemplary embodiment of the present disclosure.

Under the 90% RH condition, before the dehumidification layer is etched, the reaction rate for the moisture of the humidity sensor is 122 seconds and after the dehumidification layer is etched, the reaction rate for the moisture of the humidity sensor is 40 seconds. That is, it may be appreciated that after the dehumidification layer is etched, the reaction rate for the moisture of the humidity sensor may be three times faster than the case in which the dehumidification layer is not etched.

When the dehumidification layer is etched, it is exposed to a larger amount of moisture, such that the moisture is sensed within a faster time than the humidity sensor in which the moisture sensing layer is not etched.

Figure 13:
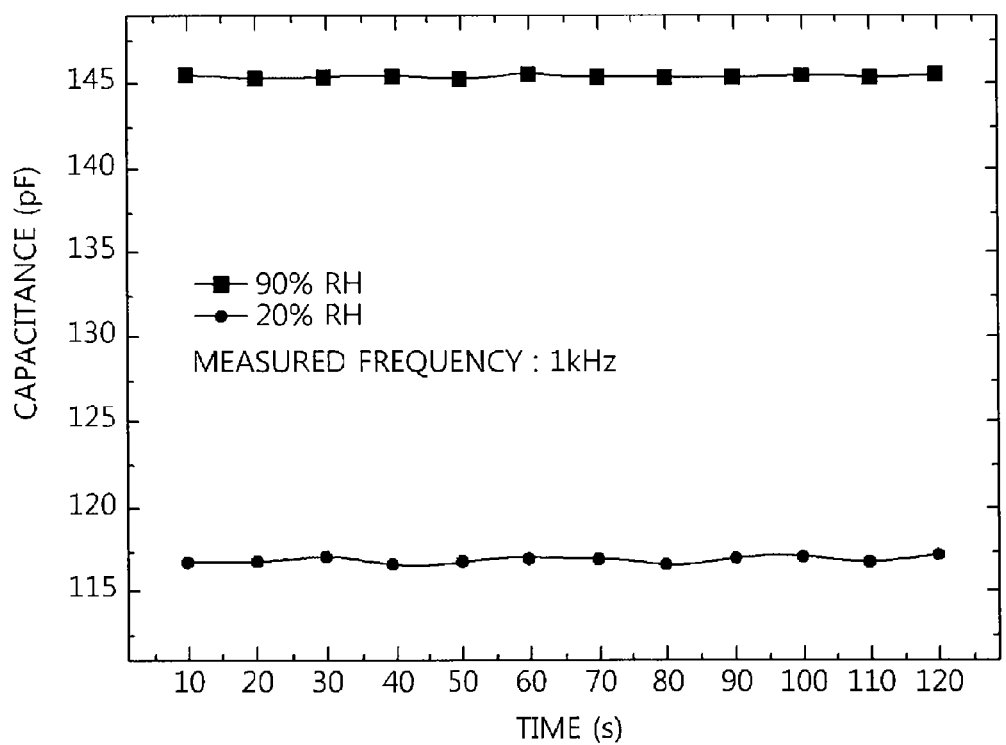

FIG. 13 shows reproducibility of a device according to the relative humidity of the capacitive humidity sensor according to an exemplary embodiment of the present disclosure.

It may be appreciated that the humidity sensor has very excellent reliability since the constant capacitance is shown as time passed.

Figure 14:
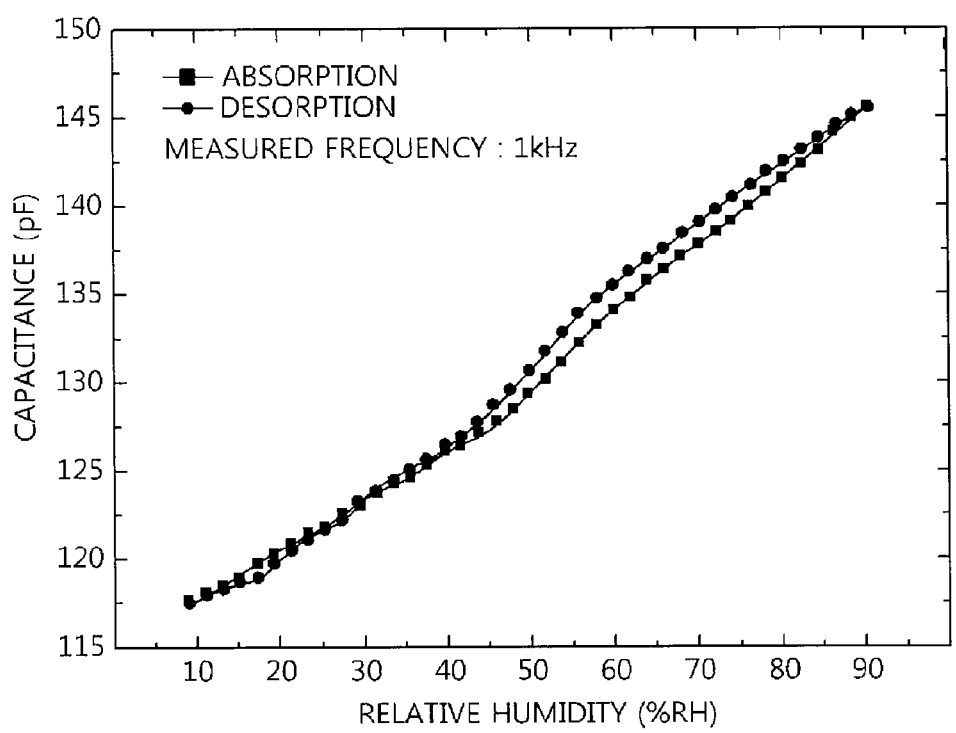

FIG. 14 shows capacitance according to the adsorption and desorption for the moisture of the capacitive humidity sensor according to an exemplary embodiment of the present disclosure.

Linear characteristics in which the capacitance is constantly increased and reduced according to the increase and reduction in the amount of moisture are shown. That is, when the humidity is increased or reduced based on the specific relative humidity, it may be appreciated that the capacitive humidity sensor according to the present disclosure has the high reliability by showing the same capacitance.

While this disclosure has been described in connection with what is presently considered to be practical exemplary embodiments, it is to be understood that the disclosure is not limited to the disclosed embodiments, but, on the contrary, is intended to cover various modifications and equivalent arrangements included within the spirit and scope of the appended claims.

What is claimed is:

1. A capacitive humidity sensor, comprising:
   an ROIC substrate that includes an electrode pad;
   a metal layer that is formed on the ROIC substrate and patterned to partially expose the electrode pad;
   an insulating layer that is formed on the metal layer and patterned to partially expose the electrode pad;
   a lower electrode layer that is formed on the insulating layer;
   a dehumidification layer formed on the lower electrode layer that is etched so as to expand its surface area;
   an upper electrode formed on the dehumidification layer; and
   a connection layer that is formed on the exposed electrode pad and contacts each of the lower electrode layer and the upper electrode layer with the electrode pad.

2. The capacitive humidity sensor of claim 1, wherein the upper electrode layer is formed on the region which is not etched in the dehumidification layer.

3. The capacitive humidity sensor of claim 2, wherein the dehumidification layer and the upper electrode layer are patterned in a comb or branch shape.

4. The capacitive humidity sensor of claim 1, wherein 30% to 70% of the thickness of the dehumidification layer is etched.

5. The capacitive humidity sensor of claim 1, wherein the dehumidification layer is made of a polyimide-based polymer.

6. The capacitive humidity sensor of claim 1, wherein the lower electrode layer is formed on the insulating layer that is not patterned.

7. A manufacturing method of a capacitive humidity sensor, the method comprising:
   forming a metal layer on an ROIC substrate including an electrode pad;
   forming an insulating layer on the metal layer;
   patterning the insulating layer and the metal layer to partially expose the electrode pad;
   forming a lower electrode layer on the insulating layer;
   forming a dehumidification layer on the lower electrode layer;
   forming and patterning an upper electrode layer on the dehumidification layer; and etching the dehumidification layer by using the patterned upper electrode layer as a mask.

8. The method of claim 7, wherein the dehumidification layer is made of a polyimide-based polymer.

9. The method of claim 7, wherein the upper electrode layer is formed by being patterned in a comb or branch shape.

10. The method of claim 7, wherein the etched dehumidification layer is formed by etching 30% to 70% of a thickness thereof.

11. The method of claim 7, wherein the lower electrode layer is formed on the insulating layer that is not patterned.

* * * * *